US011133165B1

(12) United States Patent
Ragland et al.

(10) Patent No.: US 11,133,165 B1
(45) Date of Patent: Sep. 28, 2021

(54) EXTRACTING AND ANALYZING TRAPPED GASSES IN A GLASS SAMPLE

(71) Applicant: Owens-Brockway Glass Container Inc., Perrysburg, OH (US)

(72) Inventors: Daniel Ragland, Perrysburg, OH (US); Brian Coburn, Perrysburg, OH (US); Todd Coleman, Wayne, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 105 days.

(21) Appl. No.: 16/668,103

(22) Filed: Oct. 30, 2019

(51) Int. Cl.
| | |
|---|---|
| *H01J 49/04* | (2006.01) |
| *G01N 1/00* | (2006.01) |
| *H01J 49/24* | (2006.01) |
| *G01N 33/38* | (2006.01) |
| *G01N 1/28* | (2006.01) |

(52) U.S. Cl.
CPC ........ *H01J 49/0495* (2013.01); *G01N 33/386* (2013.01); *H01J 49/0459* (2013.01); *H01J 49/24* (2013.01); *G01N 1/286* (2013.01)

(58) Field of Classification Search
None
See application file for complete search history.

(56) References Cited

U.S. PATENT DOCUMENTS

| | | | | |
|---|---|---|---|---|
| 3,387,961 | A | * | 6/1968 | Buehl ...................... B29D 5/10 65/32.5 |
| 4,269,507 | A | | 5/1981 | Allen et al. |
| 4,587,834 | A | | 5/1986 | Fisher |
| 5,224,658 | A | | 7/1993 | Smith |
| 5,286,651 | A | * | 2/1994 | Smith .................. G01N 33/241 436/32 |
| 5,365,771 | A | | 11/1994 | Gysi et al. |
| 5,772,714 | A | | 6/1998 | Sato et al. |

(Continued)

FOREIGN PATENT DOCUMENTS

| | | | | | |
|---|---|---|---|---|---|
| JP | 05231999 | A | * | 9/1993 | ............... G01N 1/28 |
| JP | 2007149681 | | | 6/2007 | |
| PL | 410738 | A1 | * | 7/2016 | ............. G01N 30/04 |

OTHER PUBLICATIONS

Neerman et al., "Sampling and Analysis of Bubbles in Glass by mass spectrometry", Analyical chemisty 1959 (Year: 1959).*

(Continued)

*Primary Examiner* — Michael J Logie

(57) ABSTRACT

A system for carrying out gas chromatography/mass spectroscopy (GC/MS) on gasses trapped in glass solidified from molten glass includes a glass sample vacuum chamber having a gas inlet, a gas outlet, and an introduction port for receiving the glass sample; a crushing tool for crushing the glass sample; a gas sample vacuum chamber disposed in downstream fluid communication with the glass sample vacuum chamber; a supply of carrier gas in fluid communication with the glass sample vacuum chamber; a GC/MS analyzer in downstream fluid communication with the gas sample vacuum chamber; an injector in fluid communication between the GC/MS analyzer and the gas sample vacuum chamber and for injecting the gas sample into the GC/MS analyzer; a gather valve in fluid communication between the glass and gas sample vacuum chambers; and a booster in fluid communication with the gas sample vacuum chamber.

18 Claims, 3 Drawing Sheets

(56) References Cited

U.S. PATENT DOCUMENTS

2018/0067091 A1\* 3/2018 Burkhalter ......... G01N 33/0016
2018/0195383 A1\* 7/2018 Smith ................. H01J 49/0422

OTHER PUBLICATIONS

Bryan et al. "Gas Chromatographic Identification of Major Constituents of Bubbles in Glass", Analytical Cehmistry, 1962 (Year: 1962).\*
Andrawes et al., "Gas chromatographic analysis of volatiles in fluid and gas inclusions" 1984 (Year: 1984).\*
Jorge et al., "Analysis of Volatiles in Fluid inclusions by direct online crushing mass spectrometry", J. Braz, Chem. Soc. 2011 (Year: 2011).\*
Richard L. Snick, et al., "Mass Spectrometric Analysis of Bubbles in Glass", Journal of the American Ceramic Society, vol. 65, No. 12, Dec. 1982, pp. 594-597.

\* cited by examiner

EXTRACTING AND ANALYZING TRAPPED GASSES IN A GLASS SAMPLE

This patent application discloses devices and methods to analyze glass compositions. More particularly, this application discloses devices and methods to analyze trapped gas content in a glass composition.

BACKGROUND

Glass products have long been made from a pre-formulated feedstock (also sometimes termed a glass batch) that is charged into a glass furnace and melted to produce molten glass for subsequent formation into a desired glass product. In the feedstock, virgin raw material ingredients—e.g., soda ash and limestone for soda-lime-silica glass—are carbonate-containing materials that, when melted, release carbon dioxide ($CO_2$). Depending on a desired composition of the desired glass product, various other additive materials can evolve other types of gasses. For example, evolution of carbon dioxide and other gasses during the feedstock melting introduces bubbles in the resultant molten glass, which, in turn, can cause an undesirable bubble in the glass product. If the gasses trapped in the molten glass are known, it is possible to optimize the glass forming process to reduce these bubbles. However, without knowing what types of gasses are forming during glass manufacturing, it is difficult to reduce the resultant bubbles.

BRIEF SUMMARY OF THE DISCLOSURE

The present disclosure embodies a number of aspects that can be implemented separately from or in combination with each other.

In accordance with one aspect of the disclosure, there is provided a system for carrying out GC/MS on gasses trapped in a glass sample solidified from molten glass. The system includes (1) a glass sample vacuum chamber having a gas inlet, a gas outlet, and an introduction port for receiving the glass sample; (2) a crushing tool for crushing the glass sample; (3) a gas sample vacuum chamber disposed in downstream fluid communication with the glass sample vacuum chamber, (4) a supply of carrier gas in fluid communication with the glass sample vacuum chamber; (5) a GC/MS analyzer in downstream fluid communication with the gas sample vacuum chamber for analyzing a released gas sample; (6) an injector in fluid communication between the GC/MS analyzer and the gas sample vacuum chamber and for injecting the gas sample into the GC/MS analyzer; (7) a gather valve in fluid communication between the glass and gas sample vacuum chambers; and (8) a booster in fluid communication with the gas sample vacuum chamber for pressure boosting the gas sample.

In an illustrative method of operation, the system is evacuated, the gather valve is closed, the glass sample vacuum chamber is provided with carrier gas, and the glass sample is crushed to release the gasses trapped therein. Thereafter, the gather valve is opened to transfer the released gas sample into the gas sample vacuum chamber, the gas sample vacuum chamber is boosted with carrier gas, and the gas sample and carrier gas are then injected into the GC/MS analyzer.

In accordance with another aspect of the disclosure, there is provided a method for carrying out gas chromatography/mass spectroscopy (GC/MS) on gasses trapped in glass solidified from molten glass. The method includes the steps of (1) loading a glass sample into a glass sample vacuum chamber; (2) pressurizing the glass sample vacuum chamber having the glass sample and a gas sample vacuum chamber downstream of the glass sample vacuum chamber; (3) isolating the glass sample vacuum chamber from the gas sample vacuum chamber by closing a gather valve located between the glass and gas sample vacuum chambers; (4) supplying the glass sample vacuum chamber with a first supply of carrier gas; (5) crushing the glass sample to generate a gas sample. After the gas sample is generated, the method further includes (6) opening the gather valve to transfer the gas sample into the gas sample vacuum chamber; (7) pressure boosting the gas-sample in the gas sample vacuum chamber with a second supply of carrier gas; and (8) injecting the pressure boosted gas sample into a GC/MS analyzer.

BRIEF DESCRIPTION OF THE DRAWINGS

The disclosure, together with additional objects, features, advantages and aspects thereof, will be best understood from the following description, the appended claims, and the accompanying drawings, in which:

DETAILED DESCRIPTION

In manufacturing glass containers and other glass products, melting of feedstock materials typically evolves various gasses that can affect the manufactured glass products. Gas chromatography/mass spectrometry (GC-MS) is an analytical method to determine the gasses present in a gas sample.

First, gas chromatography utilizes a capillary column. The column separates out different gaseous components in a composition based on their affinity for a stationary phase of the column versus a mobile phase of the column.

Once the components are separated, a mass spectrometer downstream of the column can determine the composition of the components based on their mass-to-charge ratio. In this second step, the gaseous components are subjected to an electric or magnetic field to study their amount of deflection in this field. This deflection or signal is used to determine the composition of the components. Even in the case that two or more components travel through the capillary column at the same time (e.g., co-eluting off the column), the mass spectrometer can differentiate between these components based on their different mass-to-charge ratios.

In particular, GC-MS can be useful to determine the composition of gasses trapped in a glass sample. During glass manufacturing, molten glass often retains voids or bubbles containing trapped gasses that form during melting of the feedstock materials. To reduce the occurrence of these trapped gasses, it can be beneficial to know their composition. While GC-MS is a useful tool for determining compositions of the gasses trapped in various glass samples, current GC-MS systems often analyze only small samples containing only one bubble. It is more accurate to use a larger glass sample and analyze two or more bubbles.

Figure 1:
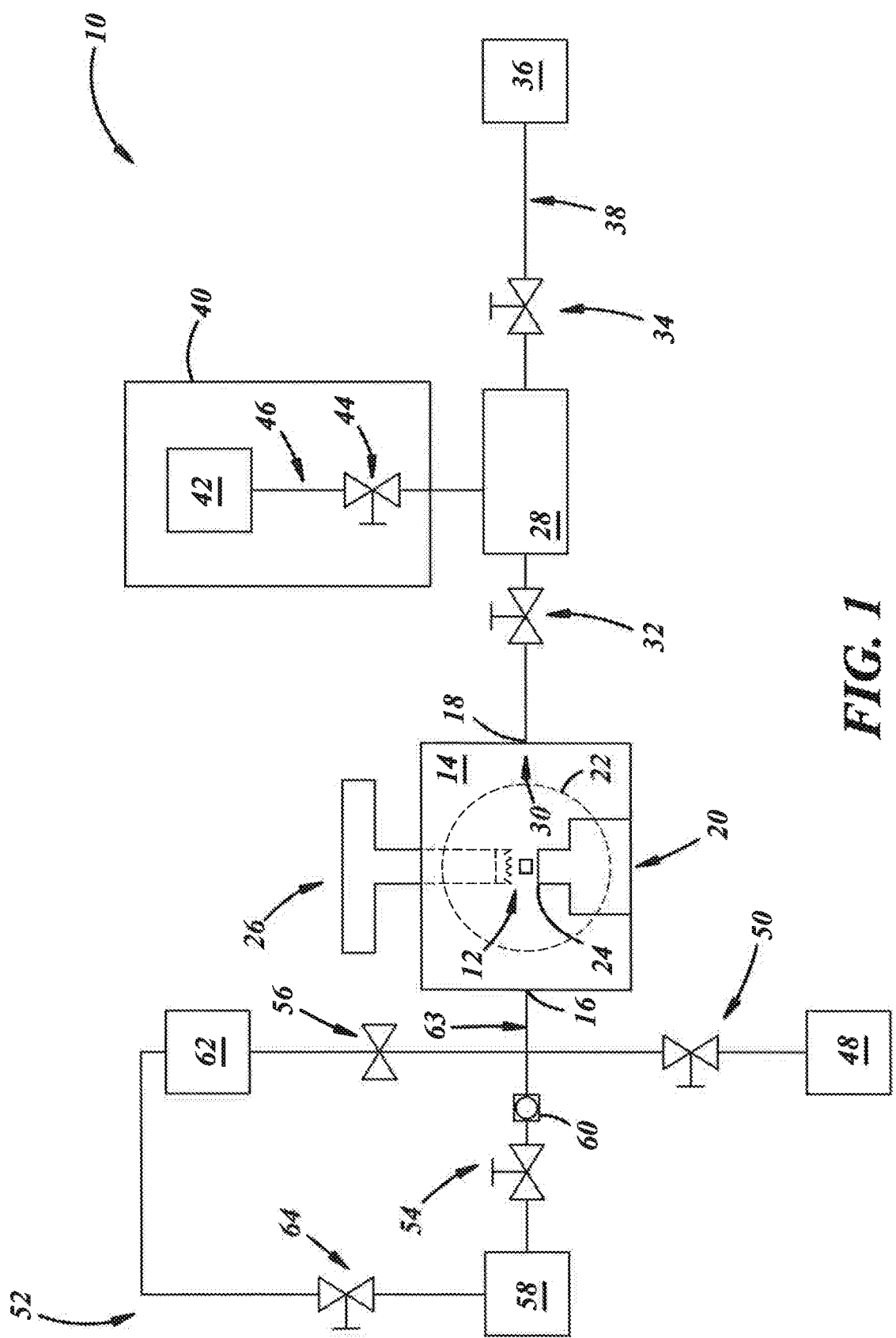
FIG. 1 is a schematic drawing of a system 10 for carrying out gas chromatography (CG) and/or mass spectroscopy (MS) in accordance with an illustrative embodiment of the present disclosure.

FIG. 1 depicts a schematic drawing of a system 10 for carrying out gas chromatography (CG) and/or mass spectroscopy (MS) in accordance with an illustrative embodiment of the present disclosure. A glass sample 12 is loaded in a glass sample vacuum chamber 14. The glass sample vacuum chamber 14 has a gas inlet 16, a gas outlet 18, and an introduction port 20 for receiving the glass sample 12. The glass sample vacuum chamber 14 optionally includes a window 22 to view the glass sample 12 when it is in the chamber 14. In the depicted example, the introduction port 20 is an opening that accommodates and is sealed with an anvil. The anvil has a sample receptacle 24 to support the glass sample 12. The anvil can be removed to introduce the glass sample 12 and reattached or redisposed in the glass sample vacuum chamber 14 to provide a support for the glass sample 12 as it is being crushed. Of course, other types of sample supports known in the art are possible for the glass sample 12.

The sample receptacle 24 can simply be a stage or surface for holding the glass sample 12. Alternatively or additionally, the sample receptacle 24 can have various components for containing the glass sample 12, such as walls, surfaces (being linear or nonlinear), various materials, and the like. FIG. 1 depicts the sample receptacle 24 forming a space having a volume for holding the glass sample 12 of at least three quarters (¾) of a cubic inch. The volume of the space allows the glass sample 12 to be similarly sized to fill in the space. A glass sample 12 being about three quarters (¾) of a cubic inch should contain two or more voids having trapped gasses that were formed during manufacturing of the glass sample 12 from the molten glass. In some cases, the two or more voids will also be isolated from each other so that they form a closed cell porosity in the glass sample 12.

A closed cell porosity is denser when compared to an open cell porosity, and more common in glass manufacturing. Because the cells are isolated from each other, they may contain different compositions of trapped gasses, possibly depending on when they were formed. A sample containing at least some or a large amount of closed cell porosity will have many voids, which may contain the same trapped gasses or different compositions of trapped gasses. Being able to analyze many different gasses at once allows a system user or operator to learn more about the overall profile of gasses being evolved during manufacturing than analyzing a single void with one composition of trapped gasses.

The glass sample vacuum chamber 14 is removably attached to a crushing tool or ram 26 for crushing the glass sample 12. In this example, the crushing tool 26 is threadably attached to the top of the glass sample vacuum chamber 14; however, it is possible to design the crushing tool 26 so that it is introduced into the glass sample vacuum chamber 14 at another location (e.g., side walls) and/or in another way (e.g., through a non-threaded entry). The crushing tool 26 can be operated manually by the system operator or user. Additionally or alternatively, the crushing tool 26 may be automatically driven by a crushing actuator, being part of the system 10. The crushing actuator can be a motor that causes movement, hydraulically, pneumatically, electrically, thermally, or mechanically. The motor takes a source of energy and converts it into motion of the crushing tool 26.

The system 10 further includes a gas sample vacuum chamber 28 disposed in downstream fluid communication with the glass sample vacuum chamber 14. The glass and gas sample vacuum chambers 14, 28 are fluidly coupled so that the glass sample vacuum chamber 14 creates a gas sample 30 to be analyzed and the gas sample vacuum chamber 28 receives the generated gas sample 30 prior to its analysis. A sample transfer valve or gather valve 32 is in fluid communication between the glass and gas sample vacuum chambers 14, 28. In FIG. 1, the gather valve 32 is positioned between the glass and gas sample vacuum chambers 14, 28 so that the fluid pathway between these two chambers can be either open or closed, or otherwise adjusted between open and closed positions.

An injector 34 is disposed downstream of the gas sample vacuum chamber 28 and in fluid communication between a GC/MS analyzer 36 and the gas sample vacuum chamber 28. The injector 34 can be a valve, needle, or closable port for injecting the generated gas sample 30 into the GC/MS analyzer 36. As depicted in FIG. 1, the injector 34 may be connected to an injection line 38 that connects to the GC/MS analyzer 36. The GC/MS analyzer 36 is in downstream fluid communication with the gas sample vacuum chamber 28 for analyzing the released gas sample 30.

Before the gas sample 30 is injected into the GC/MS analyzer 36, it is optionally pressure boosted with a booster 40, being in fluid communication with the glass and gas sample vacuum chambers 14, 28. The booster 40 includes its own supply of carrier or booster gas 42 and a booster valve 44 so that the carrier gas from the supply of carrier gas 42 can travel through a booster line 46, through the booster valve 44, and into the gas sample vacuum chamber 28 to pressure boost the gas sample 30. Gas sample 30 is pressure boosted to a target pressure before the gas sample 30 is injected into the GC/MS analyzer 36.

The booster 40 can provide the advantage of moving all of the gas sample 30 in a short amount of time onto the capillary column of the GC/MS analyzer 36. If the gas sample 30 was not pressure boosted with the booster 40, it may not be concentrated enough to yield a sufficient signal and/or would take a long time to load into the GC/MS analyzer 36. The booster 40 can load the beginning or head of the capillary column with a sufficient amount of the gas sample 30 in a respectively sufficient time to yield a signal from the GC/MS analyzer 36 to determine what gasses are in the gas sample 30.

The system 10 includes a separate, main supply of carrier gas 48 connected to a supply valve 50 to inject a flow of a carrier gas into the system 10. In FIG. 1, the supply of carrier gas 48 is in fluid communication with the glass sample vacuum chamber 14 to move the generated gas sample 30 through the system 10. The carrier gas in either of the main, or first, supply 48 or the booster, or second, supply 42 can be any suitable gas, including noble gasses such as helium, neon, argon, an unreactive fluid, or any fluid to create a carrier through the various pipes, passageways, and lines of the system 10.

The supply of carrier gas 48 is further in fluid communication with a vacuum assembly 52 of vacuum valves and pumps to generate the appropriate fluid pressure in the system 10 and/or move the gas sample 30. For example, the vacuum assembly 52 includes a first vacuum valve 54 and a second vacuum valve 56. The first vacuum valve 54 is connected to a first pump 58 (e.g., a vane pump) and is operable to generate a first pressure in the system, pressurizing the glass sample vacuum chamber to about $10^{-3}$ torr. In this context, "about" or "substantially" means that a given quantity is no more than 10%, preferably no more than 5%, more preferably no more than 1%, more or less than the stated value. For example, the pressure in the glass sample vacuum chamber is no more than 10%, preferably no more than 5%, more preferably no more than 1%, more or less than $10^{-3}$ torr.

A pressure gauge 60 can sense and display the pressure in a vacuum line 63, being directly connected to the gas inlet 16 of the glass sample vacuum chamber 14. The system user or operator can read the displayed pressure and act appropriately if the pressure reading is undesirable. It will be understood by one of ordinary skill in the art that one or more pressure gauges similar to pressure gauge 60 could be positioned at any point within the system 10 to determine and display the associated pressure.

If a lower pressure is desired, the second vacuum valve 56 is connected to a second pump 62 (e.g., turbo pump) and is operable to generate a second pressure in the system 10 being lower than the first pressure, pressurizing the gas sample vacuum chamber to between $10^{-5}$ to $10^{-6}$ torr, including all ranges, subranges, and values therebetween. A backing valve 64 between the low and high pressure portions of the vacuum assembly 52 can be open when the turbo or second pump 62 is in operation. The backing valve 64 can be used for normal and/or safety operation of the second pump 62.

Through use of the vacuum assembly 52 and the carrier gas, the system 10 can be pressurized to different pressures at different times as desired during its use. It may be desirable to have different pressures in the glass and gas sample vacuum chambers 14, 28 from each other, such as a relatively lower pressure in the gas sample vacuum chamber 28 compared to the glass sample vacuum chamber 14. By creating a vacuum differential between the chambers 14, 28, at least a portion of the released gas sample 30 can be collected in the gas sample vacuum chamber 28. Further, the first or main supply of carrier gas 48 can pressurize the glass sample vacuum chamber 14 to about 4 psi, and the second or booster supply of carrier gas 42 additionally can pressurize the gas sample vacuum chamber 28 to up to about 80 psi. In one example, the second or booster supply of carrier gas 42 can pressurize the gas sample vacuum chamber 28 to between 30 to 50 psi, including all including all ranges, subranges, and values therebetween.

Further, an additional supply of carrier gas can be connected between the gas outlet 18 and the gather valve 32, which can be at a relatively higher pressure and operational when the gather valve 32 and the injector 34 are open. The additional supply of carrier gas can complete the circuit with the GC/MS analyzer 36.

As will be appreciated by those of ordinary skill in the art, various additional connecting lines, passageways, hoses, pipes, gauges, valves (including two or three way valves), displays, processors, user interfaces, and the like can be disposed at various points within system 10 in order to facilitate operation. Similarly, the system 10 can be fully automated, not requiring user or operator input to run, manual, requiring user or operator input to run, or some combination therebetween.

In operation, the glass sample 12 is first loaded into the glass sample vacuum chamber 14. This step can include removing the introduction port 20, loading the glass sample 12, and replacing the introduction port 20 to seal the glass sample vacuum chamber 14. Second, the glass sample vacuum chamber 14 containing the glass sample 12, and the gas sample vacuum chamber 28 are pressurized. In this pressurizing step, the gather valve 32 and the first vacuum valve 54 are opened to facilitate dropping the pressure in the chambers 14, 28. In one example, when the pressure reaches $10^{-3}$ torr in the glass sample vacuum chamber 14, the first vacuum valve 54 is closed and the second vacuum valve 56 is opened, allowing the chambers 14, 28 to be completely evacuated.

The pressure in the chambers 14, 28 continues to drop until it reaches between $10^{-5}$ to $10^{-6}$ torr, including all ranges, subranges, and values therebetween. When the pressure reaches about $10^{-5}$ torr in the gas sample vacuum chamber 28, the gather valve 32 is closed to isolate the glass sample vacuum chamber 14 from the gas sample vacuum chamber 28. Then, the second vacuum valve 56 is also closed.

Subsequently, the glass sample vacuum chamber 14 is supplied with the first supply of carrier gas 48. This step can include suppling the glass sample vacuum chamber 14 with helium gas to a pressure of 4 psi. At this pressure, the glass sample 12 is crushed with the crushing tool 26 to generate the gas sample 30. After completing crushing, the gather valve 32 is opened to transfer the gas sample 30 to the gas sample vacuum chamber 28. Once the gas sample 30 is in the gas sample vacuum chamber 28, the gather valve 32 is closed to isolate the gas sample vacuum chamber 28 from the upstream portions of the system 10.

The isolated gas sample 30 is then pressure boosted with the second supply of carrier gas 42 from the booster 40. In one example, helium gas from the second supply of carrier gas 42 increases the pressure of the gas sample and the gas sample vacuum chamber 28 to a pressure of about 80 psi. By moving the gas sample 30 from the glass sample vacuum chamber 14 to the separate and isolatable gas sample vacuum chamber 28, the system 10 provides an opportunity to separately change the pressure of the gas sample 30 with the booster 40 before it is injected into the GC/MS analyzer 36. Optionally, a different carrier gas or fluid could be used in the booster 40 from the main supply of carrier gas 48, which would not be possible if the system 10 did not include separate chambers 14, 28.

In addition, the gas sample vacuum chamber 28 being separated from the glass sample vacuum chamber 14 provides for a higher sample throughput through the system 10. More specifically, once the gas sample 30 is isolated in the gas sample vacuum chamber 28, a second and/or subsequent gas sample can be generated in the glass sample vacuum chamber 14. This second or subsequent gas sample can be generated more quickly than if the first gas sample 30 had to be loaded into the GC/MS analyzer 36 before a subsequent gas sample could be generated.

After pressure boosting the gas sample 30, the sample is injected into the GC/MS analyzer 36 by way of the injector 34. Through these steps, the system 10 is evacuated, the gather valve 32 is closed, the glass sample vacuum chamber 14 is provided with carrier gas, and the glass sample 12 is crushed to release the gasses trapped therein. Thereafter, the gather valve 32 is opened to transfer the released gas sample 30 into the gas sample vacuum chamber 28. The gas sample vacuum chamber 28 is boosted with carrier gas, and the gas sample 30 and carrier gas are then injected into the GC/MS analyzer 36. The composition of the gas sample 30 is subsequently analyzed in the GC/MS analyzer 36. This analysis provides the system users and operators with information on the composition of gasses trapped in a glass sample so that they may improve glass manufacturing operations and reduce the evolution of these gasses.

Figure 2:
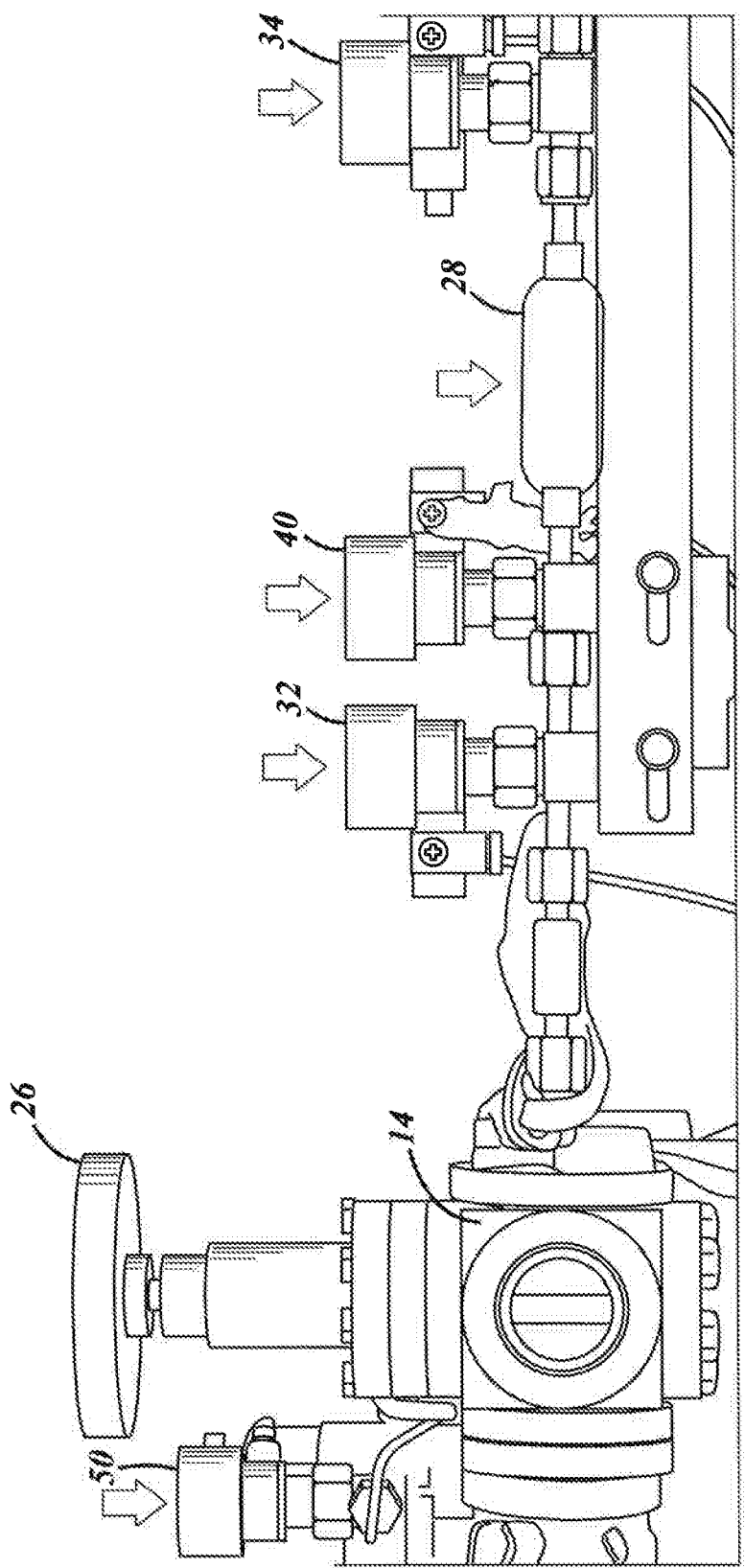
FIG. 2 is a partial view of a first set of components of the system 10 of FIG. 1 in accordance with an illustrative embodiment of the present disclosure.
Figure 3:
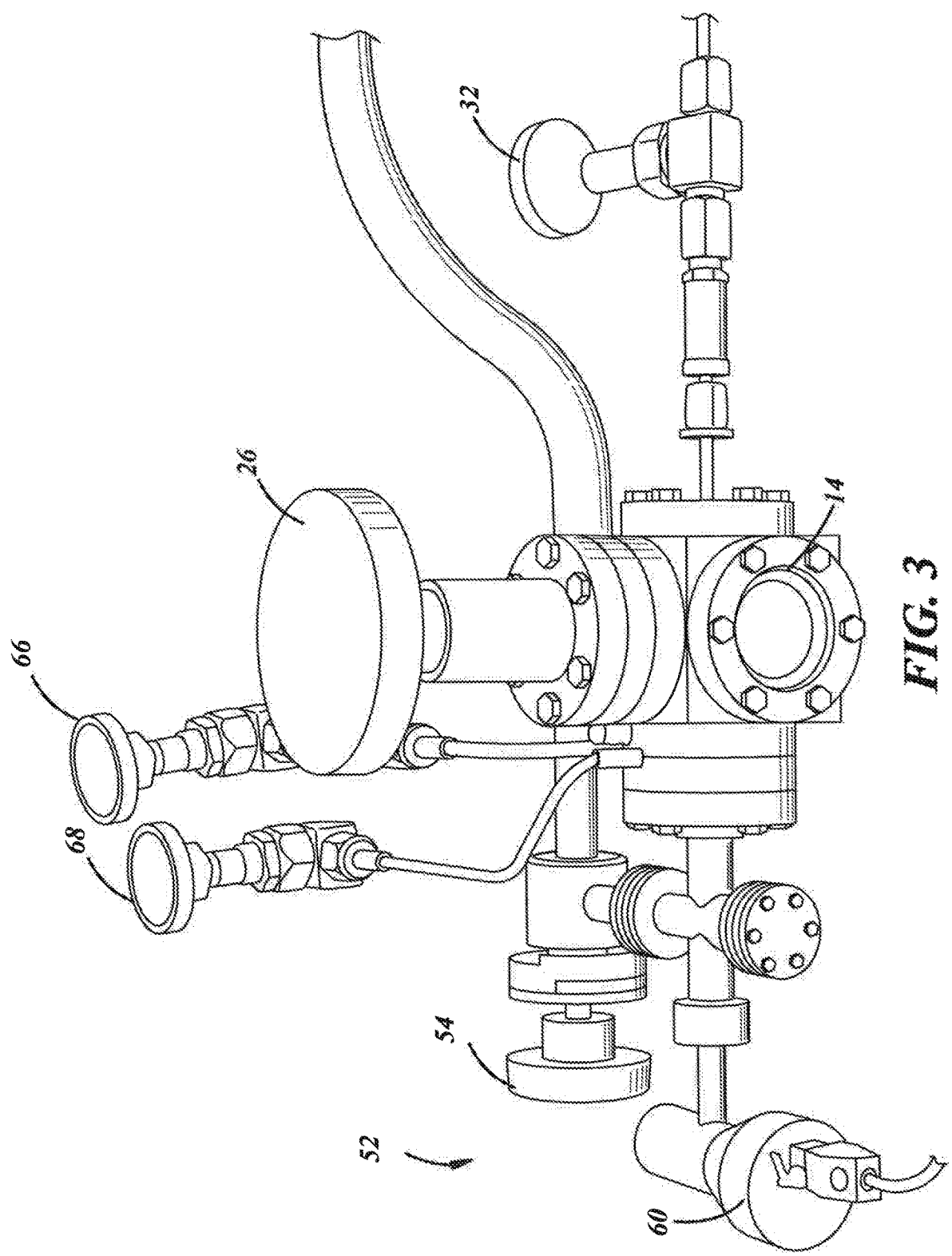
FIG. 3 is a partial view of a second set of components of the system 10 of FIG. 1 in accordance with another illustrative embodiment of the present disclosure.

FIGS. 2-3 show specific examples of some components that can be used in the system 10. For example in FIG. 2, a first set of system components includes a helium supply valve 50 allowing an introduction of helium from a first supply of carrier gas into the system. The helium supply valve 50 is upstream of the glass sample vacuum chamber 14 having the crushing tool 26 being rotatable to crush a glass sample of at least three quarters (¾) of a cubic inch. Once the glass sample is crushed, the generated gas sample moves through the system components, through the gather valve 32, to the gas sample vacuum chamber 28. The gas sample vacuum chamber 28 is in fluid communication with the booster 40, which pressure boosts the gas sample once it is in the gas sample vacuum chamber 28, and to a different pressure than the pressure in the glass sample vacuum chamber 14.

As discussed herein, the ability to pressure boost the gas sample provides the opportunity to adjust, increasing or decreasing, the pressure as necessary to prepare the gas sample for analysis in the GC/MS analyzer. Once appropriately pressurized, the gas sample is transferred through the injector 34 into the GC/MS analyzer, not shown in FIG. 2.

FIG. 3 depicts a second set of components that can be used in the system 10. In FIG. 3 various lines and valves connect the glass sample vacuum chamber 14 to the vacuum system 52, having a pressure gauge 60. The crushing tool 26 is movably received in the glass sample vacuum chamber 14 to crush the glass sample and generate the gas sample for analysis. An additional supply of carrier gas 66 can be connected to the system and/or complete the circuit with the GC/MS analyzer 36, for example between the gas outlet 18 and the gather valve 32 and/or upstream of the gather valve 32. Also, a pressure valve 68 can be connected to the glass sample vacuum chamber 14 for adding another supply of carrier gas to the glass sample vacuum chamber 14.

While FIGS. 2-3 depict only parts of the overall system, it will e understood that additional components can be added to form the overall system 10 described in FIG. 1. As can be seen in the figures, it is possible to rearrange the exact order of the system components while still maintaining fluid communication and/or upstream/downstream relationships between them as desired. Further, any of the components in any of the figures can also be added to any of the components in any of the other figures. For example, even though FIG. 1 does not specifically show the additional supply of carrier gas 66, the system 10 of FIG. 1 could include the additional supply of carrier gas 66. Any of the specific components described in any of the figures can be operated manually, by hand, and/or automatically, through use of processor(s) and/or computer(s).

There thus has been disclosed device(s) with and methods to analyze trapped gasses in glass compositions. The disclosure has been presented in conjunction with several illustrative embodiments, and additional modifications and variations have been discussed. Other modifications and variations readily will suggest themselves to persons of ordinary skill in the art in view of the foregoing discussion. For example, the subject matter of each of the embodiments is hereby incorporated by reference into each of the other embodiments, for expedience. The disclosure is intended to embrace all such modifications and variations as fall within the spirit and broad scope of the appended claims.

The invention claimed is:

1. A system for carrying out gas chromatography/mass spectroscopy (GC/MS) on gasses trapped in a glass sample solidified from molten glass, wherein the system comprises:
    a glass sample vacuum chamber having a gas inlet, a gas outlet, and an introduction port for receiving the glass sample;
    a crushing tool for crushing the glass sample;
    a gas sample vacuum chamber disposed in downstream fluid communication with the glass sample vacuum chamber;
    a supply of carrier gas in fluid communication with the glass sample vacuum chamber;
    a GC/MS analyzer in downstream fluid communication with the gas sample vacuum chamber for analyzing a released gas sample;
    an injector in fluid communication between the GC/MS analyzer and the gas sample vacuum chamber and for injecting the gas sample into the GC/MS analyzer;
    a gather valve in fluid communication between the glass and gas sample vacuum chambers; and
    a booster in fluid communication with the gas sample vacuum chamber for pressure boosting the gas sample.

2. The system of claim 1, further comprising a vacuum assembly having a first vacuum valve and a second vacuum valve, the first vacuum valve being operable to pressurize the glass sample vacuum chamber to about $10^{-3}$ torr, and the second vacuum valve being operable to pressurize the gas sample vacuum chamber to between $10^{-5}$ to $10^{-6}$ torr.

3. The system of claim 2, wherein the vacuum assembly includes a first pump connected to the first vacuum valve to generate a first pressure in the system and a second pump connected to the second vacuum valve to generate a second pressure in the system, the second pressure being lower than the first pressure.

4. The system of claim 1, wherein the supply of carrier gas includes a first supply of carrier gas, and the booster comprises a booster valve and a second supply of carrier gas such that the second supply of carrier gas is directly connected to the booster valve, and wherein the booster pressure boosts the gas sample in the gas sample vacuum chamber and as the gas sample moves from the gas sample vacuum chamber to the GC/MS analyzer.

5. The system of claim 3, wherein the first supply of carrier gas pressurizes the glass sample vacuum chamber to about 4 psi, and the second supply of carrier gas pressurizes the gas sample vacuum chamber to about 80 psi.

6. The system of claim 4, wherein the first and second supplies of carrier gas both include helium gas.

7. The system of claim 1, wherein the glass sample vacuum chamber includes a sample receptacle for holding the glass sample, the sample receptacle forming a space having a volume of at least three quarters (¾) of a cubic inch for the glass sample.

8. The system of claim 1, wherein the glass sample received in the glass sample vacuum chamber has two or more voids being isolated from each other and containing the trapped gasses, the two or more voids being formed during manufacturing of the glass sample from the molten glass.

9. The system of claim 1, wherein the crushing tool is driven by a crushing actuator.

10. The system of claim 1, wherein, in operation, the system is evacuated, the gather valve is closed, the glass sample vacuum chamber is provided with carrier gas, and the glass sample is crushed to release the gasses trapped therein and, thereafter, the gather valve is opened to transfer the released gas sample into the gas sample vacuum chamber, the gas sample vacuum chamber is boosted with carrier gas, and the gas sample and carrier gas are then injected into the GC/MS analyzer.

11. The system of claim 1, wherein the supply of carrier gas is pressurized.

12. A method for carrying out gas chromatography/mass spectroscopy (GC/MS) on gasses trapped in glass solidified from molten glass, the method comprising:
    loading a glass sample into a glass sample vacuum chamber;

pressurizing the glass sample vacuum chamber having the glass sample and a gas sample vacuum chamber downstream of the glass sample vacuum chamber;

isolating the glass sample vacuum chamber from the gas sample vacuum chamber by closing a gather valve located between the glass and gas sample vacuum chambers;

supplying the glass sample vacuum chamber with a first supply of carrier gas;

crushing the glass sample to generate a gas sample;

opening the gather valve to transfer the gas sample into the gas sample vacuum chamber;

pressure boosting the gas sample in the gas sample vacuum chamber with a second supply of carrier gas; and injecting the pressure boosted gas sample into a G/MS analyzer.

13. The method of claim 12, wherein the step of pressurizing the glass sample vacuum chamber includes pressurizing the glass sample vacuum chamber to a pressure of about $10^{-3}$ torr, and the step of isolating the glass sample vacuum chamber occurs when the gas sample vacuum chambers reaches a pressure between $10^{-5}$ to $10^{-6}$ torr.

14. The method of claim 12, wherein the first and second supplies of carrier gas both include helium gas.

15. The method of claim 12, wherein the step of supplying the glass sample vacuum chamber includes supplying the glass sample vacuum chamber to a pressure of about 4 psi, and wherein the step of pressure boosting the gas sample includes pressure boosting the gas sample to a pressure of about 80 psi.

16. The method of claim 12, further comprising the step of analyzing a composition of the gas sample with the GC/MS analyzer after the step of injecting the pressure boosted gas sample.

17. The method of claim 12, wherein the glass sample has a volume of at least three quarters (¾) of a cubic inch and two or more voids being isolated from each other and containing the trapped gasses.

18. The method of claim 12, wherein the step of crushing the glass sample includes crushing the glass sample under pressure.

\* \* \* \* \*